(12) United States Patent
Walcott et al.

(10) Patent No.: US 12,302,962 B2
(45) Date of Patent: May 20, 2025

(54) CONTEXTUAL PERSONAL PROTECTIVE EQUIPMENT

(71) Applicant: International Business Machines Corporation, Armonk, NY (US)

(72) Inventors: Aisha Walcott, Nairobi (KE); Michael S. Gordon, Yorktown Heights, NY (US); Komminist Weldemariam, Ottawa (CA)

(73) Assignee: International Business Machines Corporation, Armonk, NY (US)

( * ) Notice: Subject to any disclaimer, the term of this patent is extended or adjusted under 35 U.S.C. 154(b) by 982 days.

(21) Appl. No.: 17/128,456

(22) Filed: Dec. 21, 2020

(65) Prior Publication Data
US 2022/0192288 A1    Jun. 23, 2022

(51) Int. Cl.
| | |
|---|---|
| *A41D 13/11* | (2006.01) |
| *A41D 31/14* | (2019.01) |
| *A61B 5/00* | (2006.01) |
| *A61B 5/01* | (2006.01) |
| *F21V 33/00* | (2006.01) |

(52) U.S. Cl.
CPC .............. *A41D 13/11* (2013.01); *A41D 31/14* (2019.02); *A61B 5/01* (2013.01); *A61B 5/6803* (2013.01); *A61B 5/7282* (2013.01); *F21V 33/0008* (2013.01)

(58) Field of Classification Search
CPC .......... A43D 13/11; A43D 13/14; A61B 5/01; A61B 5/6803; A61B 5/7282; F21V 33/0008
See application file for complete search history.

(56) References Cited

U.S. PATENT DOCUMENTS

| | | | |
|---|---|---|---|
| 5,584,078 A | | 12/1996 | Saboory |
| 5,727,544 A | * | 3/1998 | Miura ..................... A41D 13/11 128/206.16 |
| 5,938,619 A | * | 8/1999 | Dogre Cuevas ..... A61B 5/0008 600/549 |
| 7,894,794 B2 | | 2/2011 | Boss et al. |
| 10,881,157 B1 | * | 1/2021 | Anderson .......... A41D 13/1107 |
| 11,160,319 B1 | * | 11/2021 | Witchey ................ A62B 18/08 |

(Continued)

FOREIGN PATENT DOCUMENTS

EP    0303056 A1    2/1989

OTHER PUBLICATIONS

Cowan et al., "The relationship of normal body temperature, end-expired breath temperature, and BAC/BrAC ratio in 98 physically fit human test subjects," NIH, Jun. 2010, 2 pages, https://www.ncbi.nlm.nih.gov/pubmed/20529457.

(Continued)

*Primary Examiner* — Katharine G Kane
(74) *Attorney, Agent, or Firm* — James L. Olsen

(57) ABSTRACT

A face mask and a method for fabricating a face mask. The face mask may comprise an air permeable membrane having an exterior surface and an interior surface, and a thermometer affixed to the exterior surface of the air permeable membrane. The air permeable membrane may be adapted to overlay a wearer's mouth and nose. The thermometer may be adapted to measure a temperature of the wearer and to allow other people in close proximity to the wearer see the temperature of the wearer at a glance.

17 Claims, 4 Drawing Sheets

(56) References Cited

U.S. PATENT DOCUMENTS

| | | | |
|---|---|---|---|
| 2008/0092909 A1 | 4/2008 | Hahne | |
| 2010/0147304 A1* | 6/2010 | Burton | A61B 5/6803 128/204.23 |
| 2013/0253809 A1 | 9/2013 | Jones et al. | |
| 2015/0353008 A1 | 12/2015 | Kline | |
| 2016/0038083 A1* | 2/2016 | Ding | A61B 5/1135 600/388 |
| 2017/0095205 A1 | 4/2017 | Abreu | |
| 2017/0128754 A1* | 5/2017 | Hou | A62B 18/02 |
| 2018/0000405 A1* | 1/2018 | Penders | A61B 8/4416 |
| 2018/0008150 A1* | 1/2018 | Hsieh | A41D 1/002 |
| 2018/0160748 A1* | 6/2018 | Yoshida | A62B 23/025 |
| 2018/0345015 A1* | 12/2018 | Straka | A41D 1/002 |
| 2019/0125011 A1* | 5/2019 | Eisenbrey | G01K 11/12 |
| 2019/0132948 A1* | 5/2019 | Longinotti-Buitoni | A61B 5/6805 |
| 2021/0038111 A1* | 2/2021 | Ahi | A61B 5/0507 |
| 2021/0081959 A1* | 3/2021 | Sweeney | G01P 13/00 |
| 2021/0330831 A1* | 10/2021 | Laty | A62B 9/006 |
| 2021/0401080 A1* | 12/2021 | Rajasekaran | A41D 13/1161 |
| 2022/0007754 A1* | 1/2022 | Kaiserman | D06M 11/83 |

OTHER PUBLICATIONS

"Use of Masks to Help Slow the Spread of COVID-19," Centers for Disease Control and Prevention, Updated Nov. 12, 2020, 4 pages, https://www.cdc.gov/coronavirus/2019-ncov/prevent-getting-sick/diy-cloth-face-coverings.html.

"Fever Fighters Forehead Thermometer Strips," Sinocare, Amazon Prime, Printed Dec. 17, 2020, 13 pages, https://www.amazon.com/Hassle-Free-Thermometer-Travel-Sized-Reusable-Children/dp/B01MQ4CHDR.

"Coronavirus: Royal Caribbean files patent for face mask," Cox Media Group National Content Desk, Updated Apr. 23, 2020, 9 pages, https://www.whio.com/news/trending/coronavirus-royal-caribbean-files-patent-face-mask/PGMGK7XTI5AXFGTKBQAVH7SF51/.

Kevlin, "Local Inventor Sees UV-Based Face Mask as Part of Solution," Allotsego.com, Cooperstown's Gerry Welch, Mar. 22, 2020, 14 pages, https://www.allotsego.com/local-inventor-sees-uv-based-face-mask-as-part-of-solution/.

Porter, "Dyson patent application imagines building an air purifier into headphones," The Verge, Feb. 4, 2020, 4 pages, https://www.theverge.com/2020/2/4/21122107/dyson-patent-application-wearable-air-purifier-headphones.

Defrancesco, "PPE Patent Pending: Next Generation Custom-fitting Masks," UConn Today, Apr. 16, 2020, 3 pages, https://today.uconn.edu/2020/04/ppe-patent-pending-next-generation-custom-fitting-masks/.

Laird et al., "The Effect on Heart Rate and Facial Skin Temperature of Wearing Respiratory Protection at Work," The Annals of Occupational Hygiene, vol. 46, Issue 2, Mar. 1, 2002, pp. 143-148, https://academic.oup.com/annweh/article/46/2/143/136411.

"Smart Face Shield," IP.Com, An IP.com Prior Art Database Technical Disclosure, IP.com No. IPCOM000262429D, IP.com Electronic Publication Date: May 29, 2020, 3 pages, https://priorart.ip.com/IPCOM/000262429.

"Our Mass Fever Screening System Scans feverish people at any venue with large human traffic," Printed Dec. 11, 2020, 2 pages, https://smartxhub.com/massive-human-temperature-screening/.

"Integrated into your security/ERP system," The Covid-19 symptoms screening solution enables real-time fever detection in public places, such as schools, commercial buildings, manufacturing industries, and transport to ensure public health, Printed Dec. 11, 2020, 3 pages.

* cited by examiner

CONTEXTUAL PERSONAL PROTECTIVE EQUIPMENT

BACKGROUND

The present disclosure relates to safety equipment, and more specifically, to personal protective equipment (PPE) with integrated sensors.

Personal protective equipment (PPE) generally refers to clothing, helmets, goggles, or other equipment designed to protect the wearer from a wide variety of hazards, including physical injury, electrocution, heat or chemicals burns, biohazard contamination, and airborne particulate matter inhalation. PPE use may help reduce the wearer's risk from the hazard to acceptable levels.

SUMMARY

According to embodiments of the present disclosure, a face mask, comprising an air permeable membrane having an exterior surface and an interior surface, and a thermometer affixed to the exterior surface of the air permeable membrane. The air permeable membrane may be adapted to overlay a wearer's mouth and nose. The thermometer may be adapted to measure a temperature of the wearer and to allow other people in close proximity to the wearer see the temperature of the wearer at a glance.

According to embodiments of the present disclosure, a method for fabricating a face mask, comprising producing an air permeable membrane having an exterior surface and an interior surface, and affixing a thermometer to the exterior surface of the air permeable membrane. The air permeable membrane may be adapted to overlay a wearer's mouth and nose. The thermometer may be adapted to measure a temperature of the wearer and to allow other people in close proximity to the wearer see the wearer's temperature at a glance.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
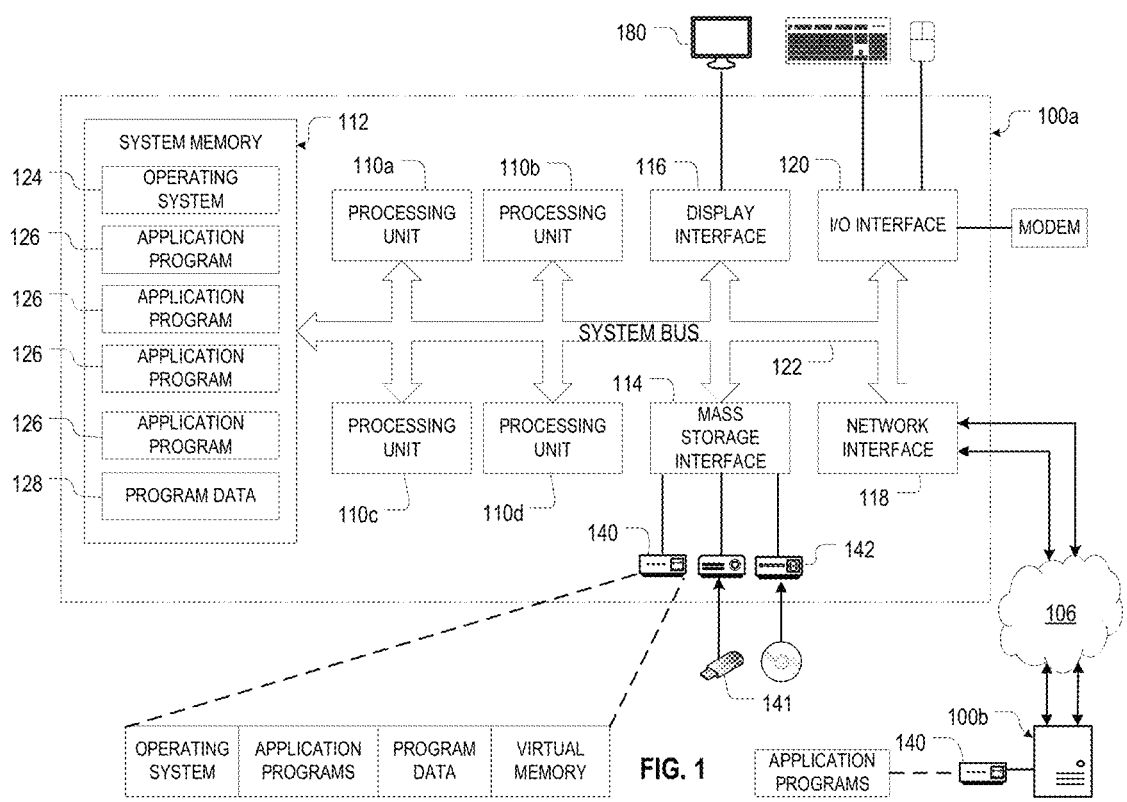
FIG. 1 illustrates an embodiment of a data processing system (DPS), consistent with some embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to safety equipment; more particular aspects relate to personal protective equipment with integrated sensors. While the present disclosure is not necessarily limited to such applications, various aspects of the disclosure may be appreciated through a discussion of various examples using this context.

Government agencies have long recommended and/or required the use of PPE for various job-related occupational safety and health purposes. Recently, however, those recommendations have expanded to include wide use for public health purposes. For example, the Centers for Disease Control (CDC) is now recommending that everyone wear a mask when in public to prevent the spread of the COVID-19 virus. This recommendation is both to protect the mask wearer and to protect the others to whom the mask wearer may come into contact, as carriers of COVID-19 may be asymptomatic, i.e., people might be contagious and not be aware of it because they show no symptoms.

PPE use, however, should be just one component of a holistic system of protection/prevention. For example, so-called social distancing of remains an important tool to help prevent the spread of diseases. Another important tool is early detection of contagious individuals. Elevated body core temperature (or fever, more specifically) may be an early symptom of a COVID-19 infection. As a result, it is now commonplace for people to measure their own body core temperature, and for employers to screen their employees, with non-contact (infrared) thermometers to detect early signs of COVID-19 by taking their temperatures. Furthermore, some retail locations, health facilities, and other sites also provide temperature checks upon entry.

Some embodiment of this disclosure may include a system and method that allows for body core temperature monitoring over the course of a day at regular intervals, or even continuously in some embodiments. Moreover, some embodiments may allow for a context in which a body core temperature reading is taken to be considered, as an individual's temperature may change over the course of a day, and thus, one reading may often be insufficient. For example, some data show that a person's true body core temperature is typically higher later in the day and lower early in the day. Similarly, measured body core temperature may be higher due to exercise, or lower due to exposure to a cold environment. Accordingly, one feature and advantage of some embodiments is the ability to collect temperature readings, and to analyze the temperature readings to determine any abnormalities and/or determine/predict a pattern of temperature changes as indicative of disease or other disorder.

Studies have shown that there exists high correlation between expired air in humans and body core temperature, specifically that exhaled air temperature was about 2° C. cooler than the body core temperature. As a result, the exhaled air temperature may be a good proxy for true body core temperature. Accordingly, some embodiments of the disclosure include an article of PPE, such as a facial mask or cloth mask, with an integrated temperature sensor that allows other people in close proximity to the PPE wearer to see the PPE wearer's temperature at a glance and to share electronic alerts of high body core temperatures. In this way, some embodiments may provide an inexpensive, disposable system and method for measuring a PPE wearer's body core temperature in public spaces. Some embodiments may further provide an inexpensive, disposable system and method to make the results of that measurement easily visible from a distance. Further, some embodiments may additionally electronically alert others of high temperature (e.g., fever) persons in close proximity (e.g., less than 10 feet away and in direct line of sight) and medium proximity (e.g., 10-50 feet away and/or not in direct line of sight).

Some embodiments of the disclosure include an article of PPE, such as a facial mask or cloth mask, that includes a liquid crystal thermometer strip ("thermometer strip"). The thermometer strip may be located on the outside surface of the PPE such that the temperature display surface is visible to anyone in front of the wearer. In facial mask or cloth mask embodiments, the temperature of the expired air from an individual's breath may transfer through the mask and be "read" by the thermometer strip, as the material is typically thin.

Embodiments utilizing thermometer strips may be desirable as the cost for the thermometer strip is comparable to the cost of the PPE alone. This feature and advantage, in turn, may enable manufactured article as a whole to be disposable. In some embodiments, the thermometer strip may be additionally replaceable. In these embodiments, the replaceable thermometer strip may be attached to and held onto the PPE surface with an adhesive material (e.g., double sided tape) or hook-and-loop fastener, inserted into a sleeve or pocket that is integrated into the PPE, etc.

In some embodiments, a wireless (e.g., Bluetooth, Wi-Fi, NFC) enabled thermometer chip may be attached to the inside of a mask in place of or in addition to the thermometer strip. The thermometer chip may communicate with a mobile application (app) executing on a PPE wearer's smart phone (or other data processing system) to record the wearer's temperature over the course of a day. Each measurement of the temperature may be time-stamped and may be treated as time series data. The removable chip may be attached to the inside of the mask via adhesives, hook-and-loop fastener, sleeve, pocket, etc., and may be transferred to new PPE, which, in turn, may help with temperature calibration across heterogeneous mask types. One feature and advantage of these embodiments is that they may allow for simple individual and crowd-based body core temperature information dissemination, using color codes or the like.

In some embodiments, the temperature may be only recorded when it exceeds a predetermined threshold. In other embodiments, the recorded temperatures may be consumed by machine learning models (e.g., LSTM Network, random forest, gradient boosting regressor, etc.) to make predictions according to the temperature of previous times. Those predictions, in turn, may be used to determine the normal temperature range of an individual at various times of day and/or as related to other activities (e.g., physical exercise, daily commutes, etc.). In this way, some embodiments may be more sensitive to changes than systems that are based on average body core temperatures of a broad group of people, or even systems based on this wearer's average body core temperature over the course of an entire day.

Another feature and advantage of some embodiments is that they allow for an opt-in method of temperature monitoring, as those opposed to such disclosure may use other forms PPE equipment.

Data Processing System

FIG. 1 illustrates an embodiment of a data processing system (DPS) 100a, consistent with some embodiments. The DPS 100a in this embodiment may be implemented as a personal computer; server computer; portable computer, such as a laptop or notebook computer, PDA (Personal Digital Assistant), tablet computer, or smart phone; processors embedded into a larger devices, such as an automobile, airplane, teleconferencing system, appliance; smart devices; or any other appropriate type of electronic device. Moreover, components other than or in addition to those shown in FIG. 1 may be present, and that the number, type, and configuration of such components may vary. Moreover, FIG. 1 only depicts the representative major components of the DPS 100a, and individual components may have greater complexity than represented in FIG. 1.

The data processing system 100a in FIG. 1 comprises a plurality of central processing units 110 a-110 d (herein generically referred to as a processor 110 or a CPU 110) connected to a memory 112, a mass storage interface 114, a terminal/display interface 116, a network interface 118, and an input/output ("I/O") interface 120 by a system bus 122. The mass storage interface 114 in this embodiment connect the system bus 122 to one or more mass storage devices, such as a direct access storage device 140, universal serial bus ("USB") storage device 141, or a readable/writable optical disk drive 142. The network interfaces 118 allow the DPS 100a to communicate with other DPS 100b over the communications medium 106. The memory 112 also contains an operating system 124, a plurality of application programs 126, and program data 128.

The data processing system 100a embodiment in FIG. 1 is a general-purpose computing device. Accordingly, the processors 110 may be any device capable of executing program instructions stored in the memory 112 and may themselves be constructed from one or more microprocessors and/or integrated circuits. In this embodiment, the DPS 100a contains multiple processors and/or processing cores, as is typical of larger, more capable computer systems; however, in other embodiments the computing systems 100a may comprise a single processor system and/or a single processor designed to emulate a multiprocessor system. Further, the processors 110 may be implemented using a number of heterogeneous data processing systems 100a in which a main processor is present with secondary processors on a single chip. As another illustrative example, the processor 110 may be a symmetric multi-processor system containing multiple processors of the same type.

When the data processing system 100a starts up, the associated processor(s) 110 initially execute the program instructions that make up the operating system 124, which manages the physical and logical resources of the DPS 100a. These resources include the memory 112, the mass storage interface 114, the terminal/display interface 116, the network interface 118, and the system bus 122. As with the processor(s) 110, some DPS 100a embodiments may utilize multiple system interfaces 114, 116, 118, 120, and buses 122, which in turn, may each include their own separate, fully programmed microprocessors.

Instructions for the operating system, applications and/or programs (generically referred to as "program code," "computer usable program code," or "computer readable program code") may be initially located in the mass storage devices 140, 141, 142, which are in communication with the processors 110 through the system bus 122. The program code in the different embodiments may be embodied on different physical or tangible computer readable media, such as the system memory 112 or the mass storage devices 140, 141, 142. In the illustrative example in FIG. 1, the instructions are stored in a functional form of persistent storage on the direct access storage device 140. These instructions are then loaded into the memory 112 for execution by the processor 110. However, the program code may also be located in a functional form on the computer readable media 142 that is selectively removable and may be loaded onto or transferred to the DPS 100a for execution by the processor 110.

The system bus 122 may be any device that facilitates communication between and among the processors 110; the memory 112; and the interfaces 114, 116, 118, 120. Moreover, although the system bus 122 in this embodiment is a relatively simple, single bus structure that provides a direct communication path among the system bus 122, other bus structures are consistent with the present disclosure, including without limitation, point-to-point links in hierarchical, star or web configurations, multiple hierarchical buses, parallel and redundant paths, etc.

The memory 112 and the mass storage devices 140, 141, 142 work cooperatively to store the operating system 124, the application programs 126, and the program data 128. In this embodiment, the memory 112 is a random-access semiconductor device capable of storing data and programs. Although FIG. 1 conceptually depicts that device as a single monolithic entity, the memory 112 in some embodiments may be a more complex arrangement, such as a hierarchy of caches and other memory devices. For example, the memory 112 may exist in multiple levels of caches, and these caches may be further divided by function, so that one cache holds instructions while another holds non-instruction data, which is used by the processor or processors. Memory 112 may be further distributed and associated with different processors 110 or sets of processors 110, as is known in any of various so-called non-uniform memory access (NUMA) computer architectures. Moreover, some embodiments may utilize virtual addressing mechanisms that allow the DPS 100a to behave as if it has access to a large, single storage entity instead of access to multiple, smaller storage entities such as the memory 112 and the mass storage device 140, 141, 142.

Although the operating system 124, the application programs 126, and the program data 128 are illustrated as being contained within the memory 112, some or all of them may be physically located on different computer systems and may be accessed remotely, e.g., via the communications medium 106, in some embodiments. Thus, while the operating system 124, the application programs 126, and the program data 128 are illustrated as being contained within the memory 112, these elements are not necessarily all completely contained in the same physical device at the same time and may even reside in the virtual memory of other DPS 100b.

The system interfaces 114, 116, 118, 120 support communication with a variety of storage and I/O devices. The mass storage interface 114 supports the attachment of one or more mass storage devices 140, 141, 142, which are typically rotating magnetic disk drive storage devices, a solid-state storage device (SSD) that uses integrated circuit assemblies as memory to store data persistently, typically using flash memory, or a combination of the two. However, the mass storage devices 140, 141, 142 may also comprise other devices, including arrays of disk drives configured to appear as a single large storage device to a host (commonly called RAID arrays) and/or archival storage media, such as hard disk drives, tape (e.g., mini-DV), writable compact disks (e.g., CD-R and CD-RW), digital versatile disks (e.g., DVD, DVD-R, DVD+R, DVD+RW, DVD-RAM), holography storage systems, blue laser disks, IBM Millipede devices, and the like.

The terminal/display interface 116 is used to directly connect one or more display units, such as monitor 180, to the data processing system 100a. These display units 180 may be non-intelligent (i.e., dumb) terminals, such as an LED monitor, or may themselves be fully programmable workstations used to allow IT administrators and customers to communicate with the DPS 100a. Note, however, that while the display interface 116 is provided to support communication with one or more display units 180, the computer systems 100a does not necessarily require a display unit 180 because all needed interaction with customers and other processes may occur via network interface 118.

The communications medium 106 may be any suitable network or combination of networks and may support any appropriate protocol suitable for communication of data and/or code to/from multiple DPS 100a, 100b. Accordingly, the network interfaces 118 can be any device that facilitates such communication, regardless of whether the network connection is made using present day analog and/or digital techniques or via some networking mechanism of the future. Suitable communication media 106 include, but are not limited to, networks implemented using one or more of the "InfiniBand" or IEEE (Institute of Electrical and Electronics Engineers) 802.3x "Ethernet" specifications; cellular transmission networks; wireless networks implemented one of the IEEE 802.11x, IEEE 802.16, General Packet Radio Service ("GPRS"), FRS (Family Radio Service), or Bluetooth specifications; Ultra-Wide Band ("UWB") technology, such as that described in FCC 02-48; or the like. Those skilled in the art will appreciate that many different network and transport protocols can be used to implement the communications medium 106. The Transmission Control Protocol/Internet Protocol ("TCP/IP") suite contains suitable network and transport protocols.

Personal Protective Equipment

FIGS. 2A-2D illustrate several embodiments of a PPE assembly 210a, 210b, 210c, 210d, using disposable facemasks as an illustrative example (hereafter referred to as disposable facemasks 210a-210d), consistent with some embodiments. For clarity, however, similar elements in FIGS. 2A-2D may not be labeled in all figures in which they appear, but will referred to by like reference numerals.

In FIGS. 2A-2D, each disposable face mask 210a-210d may have an air-permeable membrane 211, which in turn, may have an inner surface 212 typically placed adjacent to the PPE wearer's face and an outer surface 214 typically placed facing away from the PPE wearer's face. The air permeable membrane 211 may be sized and shaped to overlay the PPE wearer's mouth and nose during use. The disposable face masks 210a-210d may also include straps or elastic loops 213 and a bendable nose wire 215 adapted to secure but lightly hold the mask in position over the PPE wearer's mouth and nose.

Figure 2A:
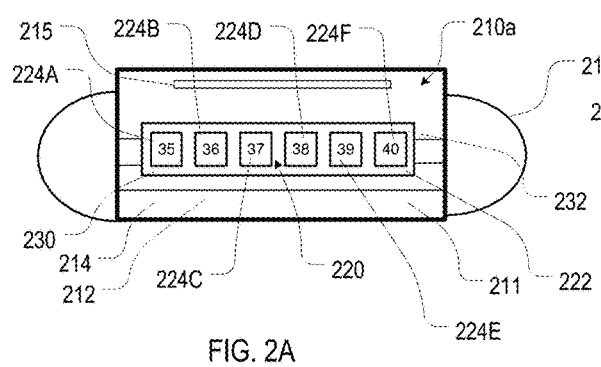
FIGS. 2A-2D illustrate several PPE assemblies, consistent with some embodiments.
Figure 2B:
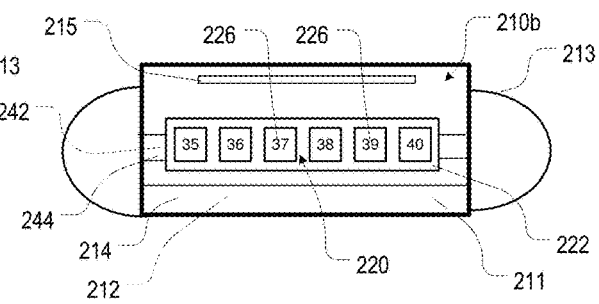
Figure 2C:
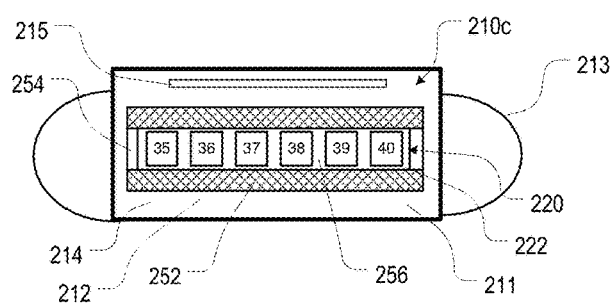

In FIGS. 2A-2C, the disposable mask embodiments 210a-201c may include a liquid crystal thermometer strip, disk, ovaloid, etc. 220 (generically, "thermometer strip"), which may be attached to the outer surface 214 of disposable mask 210 nearby the wearer's mouth (e.g., below, between the mouth and nose, etc.). The thermometer strips 220, in turn, may have a front surface 222 and a back surface 232. The front surface 222 of the thermometer strips 220 may have a plurality of different thermo-chromatic patches 224A-224F printed, or otherwise attached, thereon. Each of the plurality of different thermo-chromatic patches 224A-224F may be configured to change from a first color to a second color (e.g., from black to red) at a different, distinct temperature. For example, thermo-chromatic patch 224A may change color at about 35° C., thermo-chromatic patch 224B may change color at about 36° C., thermo-chromatic patch 224C may change color at about 37° C., thermo-chromatic patch 224D may change color at about 38° C., thermo-chromatic patch 224E may change color at about 39° C., and thermo-chromatic patch 224F may change color at about 40° C. The front surface 222 of the thermometer strip 220 may also contain a printed temperature scale 226, which may be calibrated such that the thermo-chromatic patches 224A-224F are indicative of the PPE wearer's true body core temperature (vs. the actual measured temperature at the front surface 222 of the strip 220). For example, the temperature scale 226 for patch 224A may indicate a temperature of 36° C. to account for the difference between actual body core temperature and the measured temperature at the outer surface 214 of the mask.

In FIG. 2A, the thermometer strip 220 may be attached to a first disposable mask embodiment 210a using two-sided adhesive tape 230, an adhesive coating on the back of the thermometer strip 220, etc., between a back surface 232 of the thermometer strip 220 and the outer surface 214 of the disposable mask 210. In FIG. 2B, thermometer strip 220 may be attached to a second disposable mask 210b using a matched pair of hook-and-loop fastener strips 242, 244 positioned between the back surface 232 of the thermometer strip 220 and the front surface 214 of the disposable mask 210. In FIG. 2C, the front surface 214 of a third disposable mask embodiment 210c may include a sleeve 252, which may be sized and shaped to securely but removably hold the thermometer strip 220 near the wearer's mouth. The sleeve 252 may further contain a window 254 sized and shaped so that the thermo-chromatic patches 224A-224G and the printed temperature scale 226 are visible from the front of the PPE wearer. The window 254 in some embodiments may further be covered by a transparent, flexible plastic film 256. Advantageously, in FIGS. 2A-2C, anyone in front of the PPE wearer may be able to read the thermometer strip 220 to quickly ascertain whether or not the PPE wearer is running a fever.

Figure 2D:
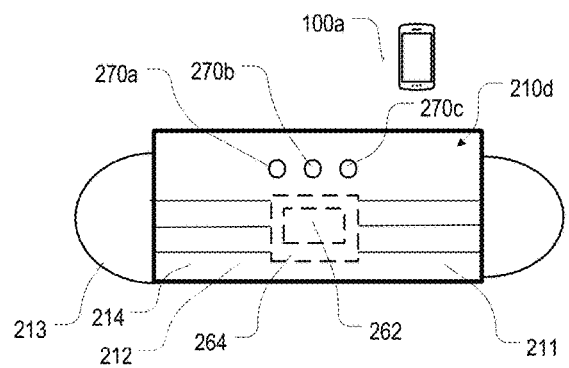

FIG. 2D illustrates a fourth disposable mask embodiment 210d, consistent with some embodiments. In FIG. 2D, a thermometer chip 262 may be attached to the disposable mask 210d, either inside the mask onto the back surface 212 or outside the mask 210 on the front surface 214. The fourth disposable mask embodiment 210d may optionally include one of the thermometer strip 220 (not shown) as described with reference to FIGS. 2A-2C.

The thermometer chip 262 in some embodiments may be adapted to measure mask wearer's 210 current temperature using an integrated temperature sensor, such as a thermocouple. The thermometer chip 262 may further be adapted to pair with one or more DPS 100a and to selectively broadcast the measured temperatures to the DPS 100a using a wireless communication interface, such as Bluetooth. This may include registering a unique identifier associated with the thermometer chip 262 with the DPS 100a. The thermometer chip 262 in FIG. 2D may be removably attached to the mask 210d using a pocket 264 sewn, or otherwise formed, into the inner surface 212 or outer surface 214 of the mask 210d. In this way, the thermometer chip 262 may be transferred from one disposable mask 210d to another.

The fourth disposable mask embodiment 210d may also include one or more external light emitting diodes (LED) 270a-270c attached to, or visible through the outer surface 214 of the mask. These LED's 270a-270c may be powered by a battery unit (not depicted) integrated into the thermometer chip 262, and may be color coded to allow different alert levels to be displayed. For example, a green colored LED 270a may be activated when the PPE wearer has a normal measured temperature, and thus, is of low risk for being a disease vector. A yellow LED 270b may be activated when the PPE wearer is of moderate risk of being a disease vector, such as: (i) only having a slightly elevated temperature; (ii) only having a more elevated temperature for a short time period; (iii) that analytics indicate that the measured temperature is otherwise to be expected; and/or (iv) that the PPE wearer has a normal temperature, but has been in close proximity to another contagious person. A red LED 270c may be activated to indicate that the PPE wearer is currently running a fever, and thus, is of high risk of being a disease vector. Advantageously, in FIG. 2D, anyone in front of the PPE wearer may be able to read the colored LEDs 270a-270c to quickly ascertain the risk of whether the PPE wearer is contagious.

In some embodiments, the thermometer chip 262 and/or the mask wearer's DPS 100a may further generate warning signals when the disposable mask 210d should be incinerated or otherwise disposed of, such as after a predetermined number of hours of use or after close exposure to another contagious PPE wearer. For example, the LCD light(s) 270 in these embodiments may all turn and remain "on" until the mask 210 is safely disposed, may blink in a characteristic patterns, etc.)

Data Collection

In some embodiments, the thermometer chip 262 may be used to communicate with others who come into close proximity to the PPE wearer. This may be done using the thermometer chip's 262 wireless communication interface and an opt-in, person-to-person data exchange protocol. In some embodiments, this protocol may include a hop network or mobile ad-hoc network (MANET) to communicate person-to-person between those individuals nearby the PPE wearer. This feature may also be used to provide alerts when entering a building, school, or even a neighborhood, based on each persons' personal profile and the number of possible cases inside the building, etc.

Figure 3:
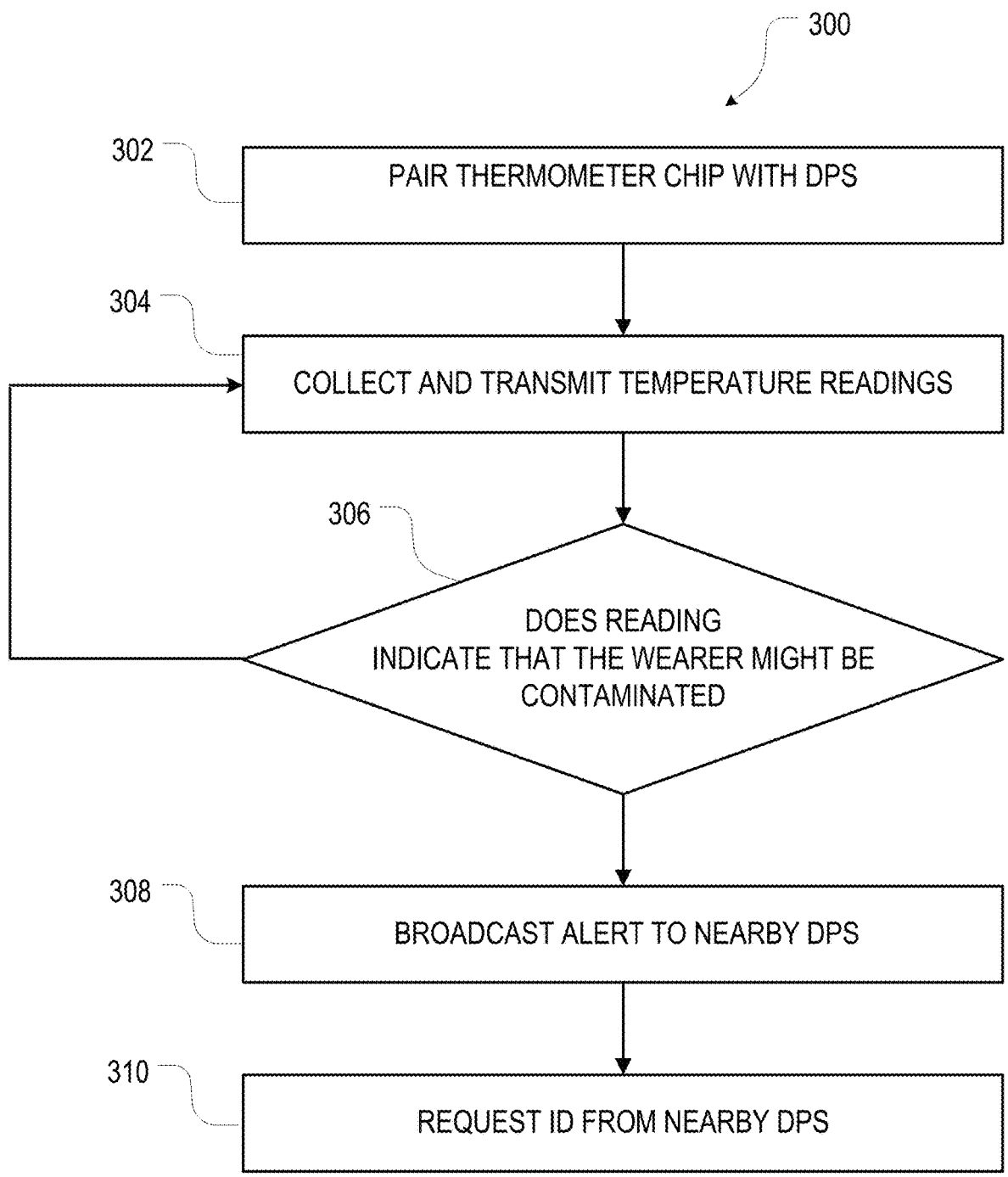
FIG. 3 is a flow chart depicting a method for triggering an alert at a mobile DPS, consistent with some embodiments.

FIG. 3 is a flow chart depicting a method 300 for triggering an alert at a mobile DPS 100a, consistent with some embodiments of the disclosure. At operation 302, the PPE wearer pairs the thermometer chip 262 with their DPS 100a. This may involve entering in an alphanumeric code printed on the thermometer chip 262, or initiating a digital handshake between the thermometer chip 262 and the DPS 100a. At operation 304, the thermometer chip 262 begins collecting periodic temperature readings and transmitting those readings to the DPS 100a. If the DPS 100a detects a reading indicating that the wearer might be contagious at operation 306, the mask wearer's DPS 100a may broadcast an alert to any other DPS 100b currently nearby at operation 308. The mask wearer's DPS 100a may then request at operation 310 that those other DPS 100b respond a unique identifier (e.g., a mobile identification number (MIN) associated with the DPS 100b), which may be stored in a data store associated with the DPS 100b and then later used to provide updates to the owner of the DPS 100b (e.g., the mask wearer's body core temperature returned to normal shortly thereafter or the mask wearer was confirmed to have COVID-19) and for contact tracing by public health officials. In this way, some embodiments may be able to both alert the PPE wearer to take action, as well as alert nearby people without disclosing any personally identifiable information of the PPE wearer. The tri-color LEDs 270a-270c may also be controlled in some embodiments.

In some embodiments, patients and health care workers in a hospital environment could opt-in to a centralized tracking system, and have consistent monitoring of temperature as they may move around the hospital by the centralized tracking system. This may allow for those in close proximity to the PPE wearer to be alerted if a patient or provider has a fever; and may provide information back to the PPE wearer to let them know their temperature is increasing or has increased beyond a threshold value. In the same way, children and teachers in a school setting can use the PPE to have continuous monitoring of temperature in classroom settings. In this way, when a student is doing physical activity, the physical activity may be detected and/or communicated to the DPS 100*a*, which will note an expected temperature increase during the period of the activity (e.g., gym class).

Data Analysis

In some embodiments, alerts may be generated using machine learning models ("ML models"), such as deep reinforcement learning algorithms adapted to learn the normal range (i.e., those experienced while healthy vs. those experienced when sick) of temperatures for the PPE wearer at various times of day and/or for various activities (e.g., in a classroom setting vs. gym class) so that deviations can be flagged more easily. For example, consider a child PPE wearer whose normal (average) temperature ranges from 98.0° F. in the morning to 99.0° F. in the evening. One day, the child's thermometer records a temperature of 99.5° F. in the afternoon and continues to rise during the course of the day to reach 100° F. in the early evening. An alert could be implemented indicating that this temperature deviates from normal and might indicate the onset of an illness. The PPE wearer's preexisting health condition is also assessed to further refine whether the temperature deviation is from a preexisting condition or not.

The machine learning models ("ML models") in some embodiments may be any software system that recognizes patterns. In some embodiments, the ML models comprise a plurality of artificial neurons interconnected through connection points called synapses. Each synapse encodes a strength of the connection between the output of one neuron and the input of another. The output of each neuron, in turn, is determined by the aggregate input received from other neurons that are connected to it, and thus by the outputs of these "upstream" connected neurons and the strength of the connections as determined by the synaptic weights.

The ML models may be trained to solve a specific problem (e.g., actual core body temperature vs. the temperature measured by the thermometer chip 262, measured core temperature time series vs. contamination risk, etc.) by adjusting the weights of the synapses such that a particular class of inputs produce a desired output. This weight adjustment procedure in these embodiments is known as "learning." Ideally, these adjustments lead to a pattern of synaptic weights that, during the learning process, converge toward an optimal solution for the given problem based on some cost function. In some embodiments, the artificial neurons may be organized into layers. The layer that receives external data is the input layer. The layer that produces the ultimate result is the output layer. Some embodiments include hidden layers between the input and output layers, and commonly there are hundreds of such hidden layers.

Figure 4:
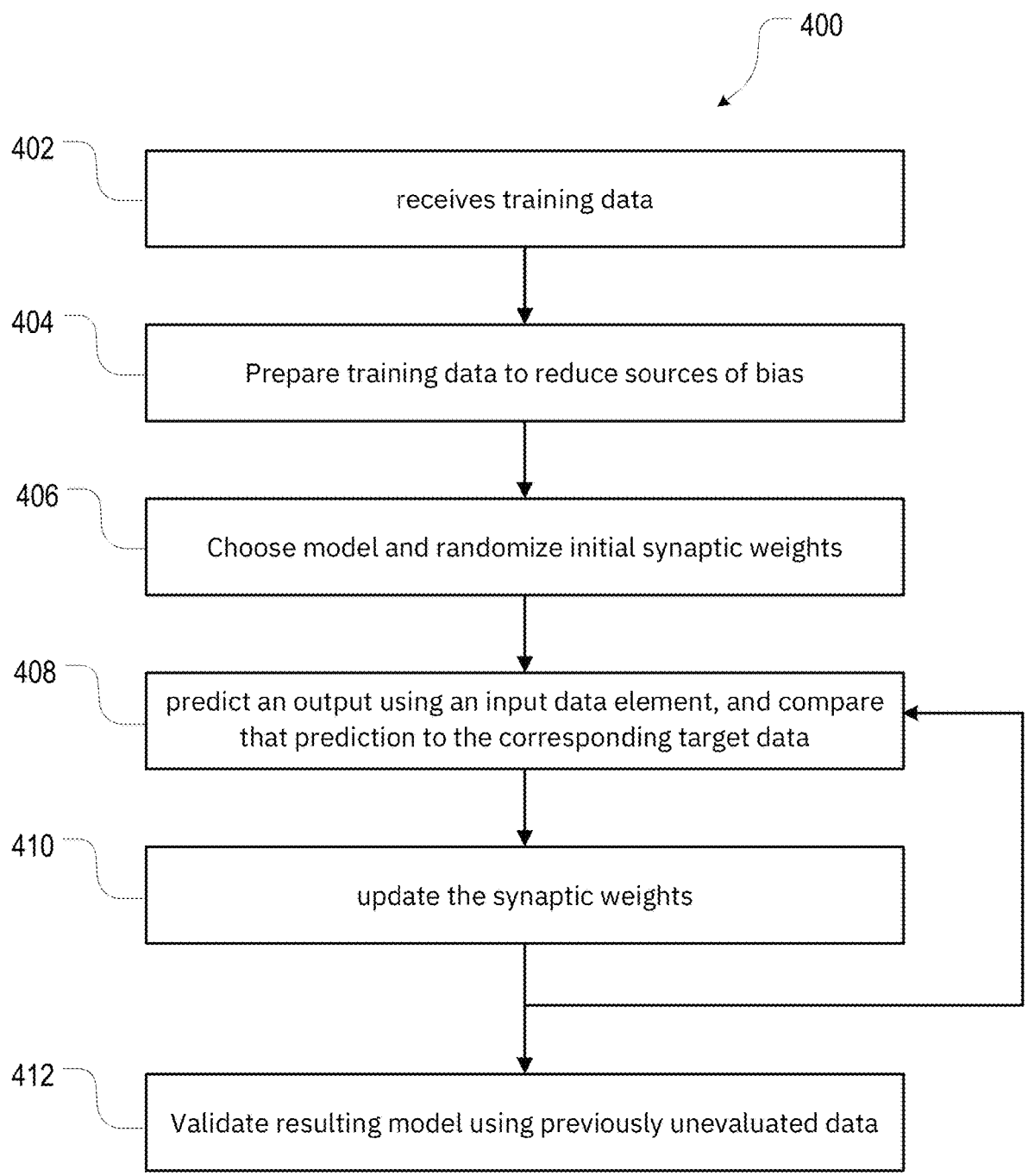
FIG. 4 is a flow chart illustrating one machine learning (ML) model training method, consistent with some embodiments.

FIG. 4 is a flow chart illustrating one ML model training method 400, consistent with some embodiments and described with reference to measured vs. actual core body temperature as an illustrative example. At block 402, the system receives training data. In this example, the input data set may include measured temperature time series collected, e.g., by the thermometer strip 220 and the target data set may include core temperature taken by conventional thermometers at regular intervals. At block 404, the training data is prepared to reduce sources of bias, typically including de-duplication, normalization, and order randomization. At block 406, a model is chosen for training and the initial synaptic weights are randomized. Depending on the underlying task, suitable models include, but are not limited to, feed-forward techniques (e.g., convolutional neural networks), regulatory feedback-based systems, radial basis function (RBF) techniques, and recurrent neural network-based techniques (e.g., long short-term memory). At block 408, the selected model is used to predict an output using the input data element, and that prediction is compared to the corresponding target data. The error (e.g., difference between the predicted value and the target value) is then used at block 410 to update the synaptic weights. This process repeats, with each iteration updating the weights, until the training data is exhausted, or the model reaches an acceptable level of accuracy and/or precision. At block 412, the resulting model may optionally be compared to previously unevaluated data to validate and test its performance. In some embodiments, the DPS 100*a* may detect and analyze the contextual situation (e.g., cultural context, location/neighborhood—some locations maybe unsafe for the identified person due to a number of reasons, time-of-the day, etc.) of the PPE wearer with high temperature and generate contextual alert with a risk level (e.g., high, medium, low). This may include directly measuring activity using integrated acceleration sensors in the DPS 100*a*, collecting a time series of locations using an integrated global positioning system receiver in the DPS 100*a*, accessing the PPE wearer's calendar, etc.

Some embodiments may further generate preventive actions using deep reinforcement learning algorithms. In these embodiments, a contextual alert from the thermometer chip 262 and/or the PPE wearer's DPS 100*a* may further trigger a backend artificial intelligence (AI) system to generate preventive actions and/or risk avoidance actions for people nearby the PPE wearer, such as an audio alerts: (i) reinforcing the need to keep the recommended safe social distance between anyone within a radius of "R"; (ii) reminding the PPE wearer and/or others avoid touching any object within a radius R of a possible contagious person; (iii) recommend routes to avoid any potentially contaminated areas (unsafe areas), identified from disease propagation models.

In some embodiments, the thermometer chip 262 may assist in contract tracing, using a ML model to analyze (reverse) correlation of historical temperature readings across multiple people and locations (extracted from the time stamps). This analysis may be coupled with temporal and go-spatial, demographics data, and mobility data, such as that available on the IBM PAIRS GEOSCOPE® platform (available from International Business Machines of Armonk, NY). The contact tracing information, in turn, may be visualized on heat map, or the like.

Computer Program Product

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

General

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Accordingly, the descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A face mask, comprising:
an air permeable membrane having an exterior surface and an interior surface, wherein the air permeable membrane is adapted to overlay a wearer's mouth and nose; and a thermometer affixed to the exterior surface of the air permeable membrane, wherein the thermometer is adapted to measure a temperature at the exterior, wherein the thermometer comprises a wireless interface adapted to communicate with an application, wherein the application comprises a machine learning model that is configured to correlate the temperature at the exterior surface with an actual body temperature of the wearer, wherein the machine learning model is trained on historical exterior surface body temperature measurements and historical core body temperature measurements, wherein the thermometer displays the actual body temperature of the wearer.

2. The face mask of claim 1, wherein the thermometer is further adapted to share alerts of high temperatures to people in close proximity to the wearer.

3. The face mask of claim 1, wherein the thermometer comprises a thermometer strip.

4. The face mask of claim 3, further comprising an adhesive layer that attaches the thermometer strip to the exterior surface of the air permeable membrane.

5. The face mask of claim 3, further comprising a hook and loop fastener that removably attaches the thermometer strip to the exterior surface of the air permeable membrane.

6. The face mask of claim 3, further comprising a sleeve formed into the exterior surface of the air permeable membrane, wherein the sleeve is adapted to hold the thermometer strip near the wearer's mouth.

7. The face mask of claim 6, further comprising a transparent window that covers the sleeve.

8. The face mask of claim 1, wherein the thermometer comprises a thermometer chip.

9. The face mask of claim 8, wherein the thermometer chip comprises the wireless interface adapted to communicate to the application executing on a smart phone.

10. The face mask of claim 9, wherein the thermometer chip further comprises an identifier that associates the thermometer chip with the application.

11. The face mask of claim 8, wherein the application is further adapted to collect a time series of temperature readings from the thermometer chip.

12. The face mask of claim 1, wherein the application is further adapted to determine an activity of the wearer.

13. The face mask of claim 12, wherein the machine learning model is further configured to correlate the temperature at the exterior surface with the actual body temperature of the wearer based on the determined activity.

14. The face mask of claim 11, wherein the machine learning model further calculates a risk level associated with the time series of temperature readings from the thermometer chip.

15. The face mask of claim 14, further comprising a light emitting diode coupled to the thermometer chip, wherein the light emitting diode activates when the calculated risk level exceeds a predetermined threshold.

16. The face mask of claim 8, further comprising a light emitting diode coupled to the thermometer chip, wherein the thermometer chip activates the light emitting diode when the actual body temperature of the wearer exceeds a predetermined threshold.

17. The face mask of claim 1, wherein the machine learning model is configured to correlate the temperature at the exterior surface with the actual body temperature of the wearer based on time of day.

* * * * *